(12) United States Patent
Kemeth et al.

(10) Patent No.: US 7,646,844 B2
(45) Date of Patent: Jan. 12, 2010

(54) METHOD FOR OPERATING A MEDICAL EXAMINATION APPARATUS AND AN EXAMINATION APPARATUS ASSOCIATED THEREWITH

(75) Inventors: Herbert Kemeth, Hausen (DE); Manfred Schönborn, Gerhardshofen (DE)

(73) Assignee: Siemens Aktiengesellschaft, Munich (DE)

( * ) Notice: Subject to any disclaimer, the term of this patent is extended or adjusted under 35 U.S.C. 154(b) by 445 days.

(21) Appl. No.: 11/639,150

(22) Filed: Dec. 14, 2006

(65) Prior Publication Data
US 2007/0154188 A1     Jul. 5, 2007

(30) Foreign Application Priority Data
Dec. 20, 2005    (DE) .................... 10 2005 061 005

(51) Int. Cl.
*A61B 6/00*    (2006.01)
(52) U.S. Cl. ............................................. 378/8
(58) Field of Classification Search ............... 378/4–20, 378/95–97, 193–198; 600/425, 428
See application file for complete search history.

(56) References Cited

U.S. PATENT DOCUMENTS

| | | | |
|---|---|---|---|
| 5,751,782 A | 5/1998 | Yoshitome | |
| 6,435,714 B1 | 8/2002 | Bruder | |
| 6,959,067 B2 * | 10/2005 | Rasche et al. | 378/8 |
| 2005/0058248 A1 | 3/2005 | Klingenbeck-Regn | |

FOREIGN PATENT DOCUMENTS

| | | |
|---|---|---|
| DE | 196 27 166 A1 | 1/1997 |
| DE | 19936679 A1 | 3/2001 |
| DE | 103 36 278 A1 | 3/2005 |

\* cited by examiner

*Primary Examiner*—Courtney Thomas

(57) ABSTRACT

Method for operating a medical examination apparatus, having an image recording device, which is moved in a rotary motion through a predetermined angular range around the patient in order to produce image recordings of a periodically moving object, with several runs being carried out by the image recording device in order to produce the image recordings and the start of the individual runs being initiated as a function of a reference signal, which represents a current movement status of the organ to be mapped, such that image recordings are produced at different radiation angles with each run.

12 Claims, 2 Drawing Sheets

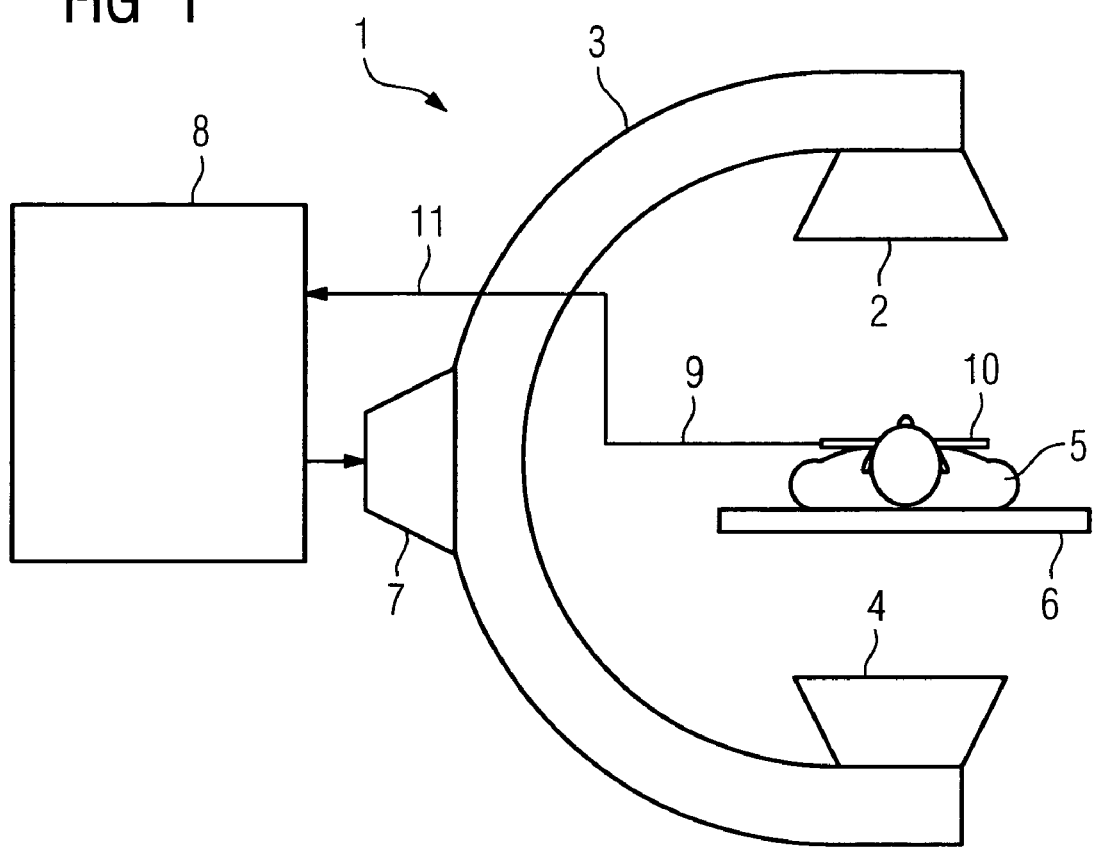

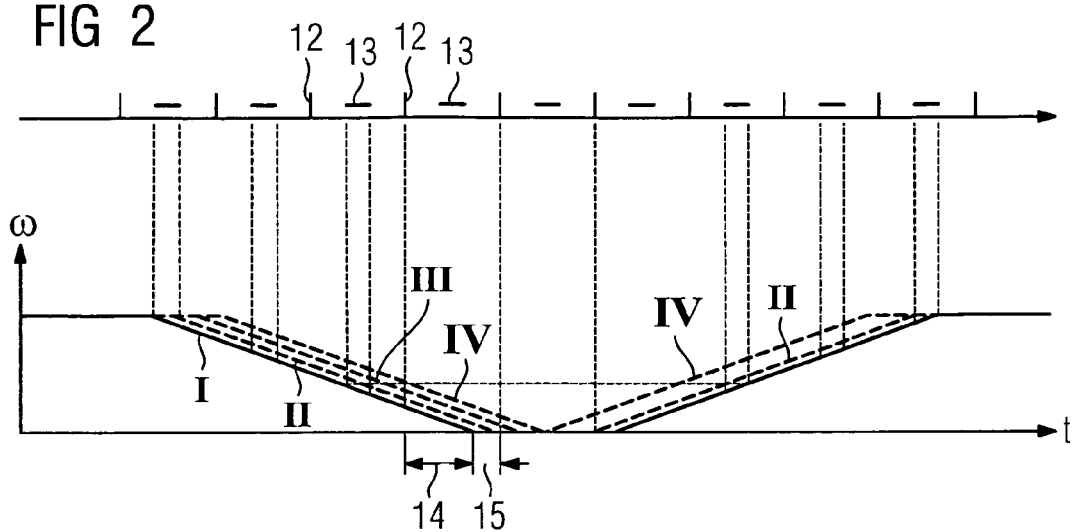
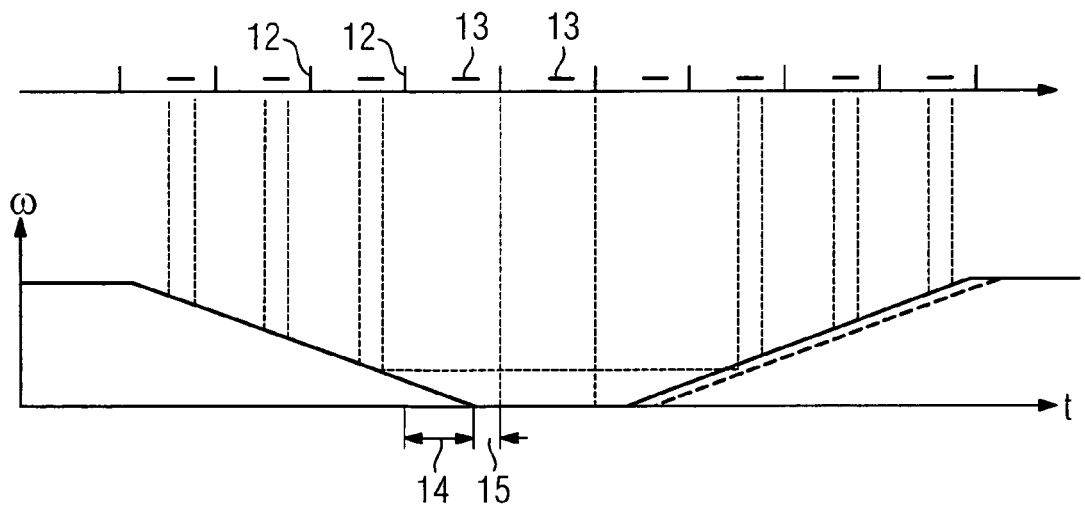

METHOD FOR OPERATING A MEDICAL EXAMINATION APPARATUS AND AN EXAMINATION APPARATUS ASSOCIATED THEREWITH

CROSS REFERENCE TO RELATED APPLICATIONS

This application claims priority of German application No. 10 2005 061 005.6 DE filed Dec. 20, 2005, which is incorporated by reference herein in its entirety.

FIELD OF INVENTION

The invention relates to a method for operating a medical examination apparatus, having an image recording device, which is moved in a rotary motion through a defined angular range around a patient in order to produce image recordings of a periodically moving organ.

BACKGROUND OF INVENTION

Recent medical technology is focusing more and more on producing 3D reconstructions of the organs of the body of a human or animal patient, since spatial representation substantially improves diagnosis possibilities. One condition for a corresponding high-quality three-dimensional representation is however that the organs do not move during the image recording. To be able to produce a 3D reconstruction of a periodically moving object, the image recording must be synchronized with the movement of the object.

US 2005/0058248 A1 describes a method for mapping an organ by means of a recording device rotating through an angle. With this method, an image recording system, e.g. an angiographic x-ray C-arm, is moved once around the patient in a rotary motion of less than 360°. The rotational speed of the rotating recording device is modulated here as a function of a reference signal, which can be an ECG signal for instance. Accordingly, the recording device is not moved at a constant speed, but is accelerated and slowed down synchronously with the heartbeat, so that the recording system is moved as quickly as possible during the phase of the cardiac cycle which is of interest but is moved as slowly as possible during the remaining phases of the cardiac cycle. This method makes heavy demands on the mechanics and control system of the examination apparatus.

DE 196 27 166 A1 discloses an x-ray computed tomography device with an x-ray tube and a detector, which rotate completely, in some instances several times in one direction, at constant speed around an object to be scanned, in order to acquire data only during specific phase segments of the movement of the object. A period and a phase are detected from R-waves in an electro-cardiographic signal.

SUMMARY OF INVENTION

An object underlying the invention is thus to specify a method, which can be realized with minimal effort.

To achieve this object, a method of the type cited in the introduction is provided in accordance with the invention whereby several runs are carried out by the image recording device in order to produce the image recordings, and the start of the individual runs is initiated as a function of a reference signal, which represents a current movement status of the organ to be mapped, such that with each run, image recordings are produced at different radiation angles.

In contrast to the prior art, the method according to the invention provides that the angular range covered, in which the image recordings are produced, is not scanned by a single run, but instead by several runs. The individual runs of the image recording device are thus synchronized here by means of the reference signal, such that during each run, the region of interest moves into another radiation angle. The method according to the invention can be implemented with conventional medical examination apparatuses with comparatively little effort, since only the controller must be adjusted and the start of the individual runs is optimally calculated and initiated for the image recordings.

The method according to the invention can be used to particular advantage when an image recording of a beating heart is produced. A 3D representation of the examined heart can then be produced from the image data.

A particularly precise resolution of the individual runs of the method according to the invention can be achieved when an ECG signal is detected as a reference signal. The individual runs can thus be controlled precisely as a function of the heartbeat, so that image recordings are produced at exactly the desired time.

The method according to the invention can be particularly efficiently implemented if the image recording device scans an angular range of less than 360° with one run and image recordings are produced during at least one forward run and during at least one return run. In this way both the forward run and the return run are used to produce image recordings, thereby keeping the overall duration of the examination to a minimum. The start of the forward run and also of the return run is initiated here in each instance precisely as a function of the reference signal.

In order to subject the patient to as little radiation exposure as possible during the implementation of the method according to the invention, provision can be made for an image recording only to be carried out within a predetermined angular range and in some instances for the radiation to be reduced or stopped outside said angular range. This is particularly expedient if the medical examination apparatus is an x-ray system.

In addition, the invention relates to a medical examination apparatus, having an image recording device, which can be moved in a rotary motion through a defined angular range around a patient in order to produce image recordings of a periodically moving organ.

With the medical examination apparatus according to the invention, the image recording device for producing image recordings is designed to automatically implement several runs, with the start of the individual runs being able to be initiated as a function of a reference signal, which represents a current movement status of the organ to be mapped, in order to produce image recordings at a different radiation angle during each run.

Expedient developments of the invention are described in the subclaims.

BRIEF DESCRIPTION OF THE DRAWINGS

Further advantages and details of the invention are explained on the basis of an exemplary embodiment with reference to the figures. The figures are schematic representations and show:

FIG. 1 a medical examination apparatus according to the invention;

FIG. 2 a first exemplary embodiment of the temporal cycle of the method according to the invention; and FIG. 3 a second exemplary embodiment of the temporal cycle of the method according to the invention.

DETAILED DESCRIPTION OF INVENTION

FIG. 1 shows an inventive medical examination apparatus 1 with an image recording device comprising an x-ray source 2, which is affixed to a C-arm 3, with the x-rays being detected by an x-ray detector 4, after having been attenuated by the body 5 of a patient. During the examination the patient is positioned on a patient support 6.

During the examination and image recording the C-arm 3 can be rotated around the body 5 of the patient in order to be able to produce image recordings at different angles. The C-arm 3 is moved by way of drive unit 7 (illustrated schematically), which is controlled by a control device 8.

The individual runs of the rotatable C-arm 3 are controlled as a function of the reference signal 9; in the exemplary embodiment shown, the reference signal 9 is an ECG signal, which is detected by a measuring device 10 and is transmitted to the control unit 8 by means of a data line 11.

FIGS. 2 and 3 clarify how the starting point is calculated for the return run in each instance.

FIG. 2 shows the temporal cycle of the method according to the invention and the calculation of the starting point for the return run.

The diagram in FIG. 2 illustrates how the starting point of the return run is calculated when the image recording is carried out in the middle of the cardiac cycle. The vertical lines on the upper horizontal scale in FIG. 2 each represent a trigger 12, which indicates the occurrence of R-spikes in the ECG signal. A horizontal marking 13 is shown between two triggers 12 symbolized by the vertical lines in each instance, said marking indicating the region of interest for the image recording. FIG. 2 shows that the region of interest (marking 13) is located in the middle of the cardiac cycle, which is bounded by the vertical lines and/or triggers 12.

The mean cardiac time which corresponds to the time between the occurrence of two consecutive R-spikes is designated with $T_h$.

N is the number of runs, in other words the sum of the forward and return runs. The temporal offset per through run is calculated from:

$$T_{Versatz} = T_h/N.$$

When calculating the start time for the return runs, the position of the two last triggers must be maintained. The trigger positions, which are achieved by the control device 8 for the motor of the drive unit 7, serve to calculate the distance from the current stop position. This value is used to decide which of the two trigger positions is correct. This trigger position, expressed as an angle, is:

$$\phi_{LT}.$$

The angle and the time for the ramp are calculated as follows:

$$\phi_{Ramp} = \omega^2/2a,$$

$$T_{Ramp} = \omega/a.$$

With the first forward run, the time from the last trigger to the stop is calculated:

$$\phi_{Stopp} = |\phi_{LT} - \phi_{act}|.$$

Here $\phi_{act}$ designates the current angle.

When $\phi_{Stopp} \leq \phi_{Ramp}$, then:

$$T_{Stopp} = \sqrt{2\phi_{Stopp}/a}$$

Otherwise:

$$T_{Stopp} = T_{Ramp} + (\phi_{Stopp} - \phi_{Ramp})/\omega,$$

this time is used for all return runs.

The wait time for the forward run is calculated as follows:

$$T_{wait} = T_{Versatz} \cdot (N-1).$$

The wait time for the return run is calculated as follows:

$$T_{wait} = T_h - T_{Stopp} - T_{Versatz} \cdot (N-1),$$

When $T_{Wait} > T_h$, then $$T_{wait} = T_{wait} - T_h,$$

when $T_{Wait} < 0$, then $$T_{wait} = T_{wait} + T_h.$$

$T_{Stopp}$ is shown as 14 in FIG. 2, this value specifying the time from the last trigger to the stop of the C-arm 3. Reference character 15 denotes the difference $T_h - T_{Stopp}$, it being necessary to wait for this time period 15 after the next trigger 12, before the return run is started, in order to carry out measurements during a return run in the same cardiac phase and during the same phase angle of the recording device.

A total of four forward runs I-IV are shown in FIG. 2, with the time shown on the horizontal axis and the angular speed of the C-arm on the vertical axis. The respective stop ramps are shown when all four runs are made in the forward direction. The individual runs would then be displaced in each instance by a quarter of the cardiac time. In the exemplary embodiment shown, the runs II and IV are intended to be executed as return runs. To this end, the stop ramps of the forward runs are mirrored and displaced into the next cardiac cycle. This results in the return runs having to begin earlier by the time $T_{Versatz}(N-1)$, as shown in the right-hand curves marked II and IV. This means that the entire angular range in the middle of the cardiac cycle is covered.

FIG. 3 shows a second exemplary embodiment of the method according to the invention, in which the image recording is carried out away from the middle of the cardiac cycle.

In accordance with FIG. 2, vertical lines are shown as triggers 12 in the upper part of FIG. 3, the horizontal markings 13 each indicating the region of the cardiac cycle of interest for the image recording. In contrast to the first exemplary embodiment, the markings 13 are however not in the middle of the cardiac cycle, but are displaced in relation thereto.

The lower part of FIG. 3 shows the angular speed ω of the C-arm shown above the time axis t.

To allow for the displacement of the region of interest which is represented by the markings 13, the return runs must be displaced by the time $T_{Offset}$. $T_{Offset}$ is a configuration value for the offset of the return runs as a percentage of the cardiac time and specifies the extent to which the scanning region has been displaced from the middle of the cardiac cycle. To displace the region temporally backward in respect of the cardiac phase, the wait time for the start of the return runs is extended by this time and calculated as follows:

$$T_{wait} = T_h - T_{Stopp} - T_{Versatz} \cdot (N-1) + T_{Offset}.$$

$T_{MV}$ is the displacement of the region of interest from the middle of the cardiac cycle, $T_{Offset}$ is thus given by:

$$T_{Offset} = 2 \cdot T_{MV}.$$

The invention claimed is:

1. A method for operating a medical examination apparatus having an image recording device, comprising:
   moving the image recording device in a rotary motion through a defined angular range around a patient in order to produce image recordings of a moving organ;
   repeating the movement of the image recording device to fulfill a plurality of runs in order to produce an image recording;
   starting an individual run based upon a reference signal that represents a current movement status of the moving organ;
   initiating each individual run such that image recordings are made from different radiation angles;
   covering an angular range of less than 360° with each run by the image recording device; and
   producing image recordings of the moving organ during at least one forward run and during at least one return run.

2. The method as claimed in claim 1, wherein the moving organ moves periodically.

3. The method as claimed in claim 1, wherein an image recording of a beating heart is produced.

4. The method as claimed in claim 1, wherein an ECG signal is measured as a reference signal.

5. The method as claimed in claim 1, wherein an image recording is only carried out within a predetermined angular range.

6. The method as claimed in claim 5, wherein a radiation source is used to emit radiation and the radiation is reduced outside an angular range predetermined for the image recording.

7. The method as claimed in claim 6, wherein the radiation is stopped outside a angular range predetermined for the image recording.

8. The method as claimed in claim 1, wherein during an image recording, that occurs within a cardiac cycle, a wait time $T_{wait}$ for the return run is calculated by $$T_{wait} = T_h - T_{Stop} - T_{Versatz} \cdot (N-1)$$

with $T_h$ being the mean cardiac time which elapses between the occurrence of two consecutive R-spikes; $T_{Stop}$ being the time from the last trigger to the stop, $T_{Versatz}$ being $T_h/N$, with N corresponding to the sum of forward and return runs.

9. The method as claimed in claim 1, wherein during the image recording, which is displaced in relation to the middle of a cardiac cycle, the wait time $T_{wait}$ for the return run is calculated by $$T_{wait} = T_h - T_{Stop} - T_{Versatz} \cdot (N-1) + T_{Offset}$$

with $T_h$ being the mean cardiac time, which elapses between the occurrence of two consecutive R-spikes, $T_{Stop}$ being the time from the last trigger to the stop, $T_{Versatz}$ being $T_h/N$, N corresponding to the sum of forward and return runs, and $T_{Offset}$ being a parameter for the displacement of the region of interest in relation to the middle of the cardiac cycle.

10. A medical examination apparatus, comprising:
   an image recording device that is configured to undergo rotary motion through a defined angular range of less than 360° per run about a patient in order to produce image recordings of a moving organ, with the image recording device automatically performing at least one forward run and at least one return run in order to produce image recordings of a region of interest of the moving organ at a different radiation angle with each run, and wherein the apparatus is configured to initiate the start of each run based on generation of a reference signal indicative of a current movement status of the moving organ.

11. The medical examination apparatus as claimed in claim 10, wherein the organ is moving periodically.

12. The medical examination apparatus as claimed in claim 10, wherein the reference signal is an ECG signal.

* * * * *

UNITED STATES PATENT AND TRADEMARK OFFICE
CERTIFICATE OF CORRECTION

| | | |
|---|---|---|
| PATENT NO. | : 7,646,844 B2 | |
| APPLICATION NO. | : 11/639150 | |
| DATED | : January 12, 2010 | |
| INVENTOR(S) | : Kemeth et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 474 days.

Signed and Sealed this

Sixteenth Day of November, 2010

David J. Kappos
*Director of the United States Patent and Trademark Office*